(12) United States Patent
Schneider et al.

(10) Patent No.: US 12,729,715 B2
(45) Date of Patent: Sep. 8, 2026

(54) BEARING ASSEMBLY OF A SWASH PLATE IN A STEERING GEAR COMPONENT AND SURGICAL INSTRUMENT

(71) Applicant: KARL STORZ SE & Co. KG, Tuttlingen (DE)

(72) Inventors: Janosz Schneider, Tuttlingen (DE); Michael Egle, Tuttlingen (DE); Dominik Längle, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 1054 days.

(21) Appl. No.: 17/869,931

(22) Filed: Jul. 21, 2022

(65) Prior Publication Data

US 2023/0031206 A1 Feb. 2, 2023

(30) Foreign Application Priority Data

Jul. 28, 2021 (DE) .................... 10 2021 119 528.4

(51) Int. Cl.
*A61B 17/29* (2006.01)
*F16C 19/50* (2006.01)
*A61B 17/00* (2006.01)

(52) U.S. Cl.
CPC ............ *F16C 19/502* (2013.01); *A61B 17/29* (2013.01); *A61B 2017/00323* (2013.01); *A61B 2017/00398* (2013.01); *A61B 2017/00845* (2013.01); *A61B 2017/2902* (2013.01)

(58) Field of Classification Search
CPC .............................. F16C 19/502; A61B 17/29
USPC .............................................................. 606/1
See application file for complete search history.

(56) References Cited

U.S. PATENT DOCUMENTS

| | | | | |
|---|---|---|---|---|
| 5,454,827 | A | 10/1995 | Aust et al. | |
| 10,105,128 | B2 | 10/2018 | Cooper et al. | |
| 2008/0188890 | A1* | 8/2008 | Weitzner | A61B 1/00165 606/205 |
| 2021/0038331 | A1 | 2/2021 | Grüner | |

FOREIGN PATENT DOCUMENTS

| | | | |
|---|---|---|---|
| CH | 558897 | A | 2/1975 |
| DE | 102019121092 | A1 | 2/2021 |

OTHER PUBLICATIONS

Office Action for corresponding German Patent Application No. 10 2021 119 528.4, mailed Mar. 3, 2022.

* cited by examiner

*Primary Examiner* — Nadia A Mahmood
(74) *Attorney, Agent, or Firm* — Jason H. Vick; Amped IP LLC

(57) ABSTRACT

An exemplary embodiment relates to a bearing assembly (40) for a swash plate (14) in a steering gear component (33), wherein the swash plate (14) is arranged such that it can rotate about an axis of rotation (10) in a radial bearing which is located in a receiving opening (330) of the steering gear component (33). The radial bearing is a sliding bearing (35) and the bearing assembly (40) has at least one axial securing device (36) which is arranged axially adjacent to a first side of the swash plate (14) and engages with the steering gear component (33). Furthermore, a surgical instrument (1) is disclosed that has this bearing assembly (40) of a swash plate (14) in a steering gear component (33).

20 Claims, 6 Drawing Sheets

Prior Art

Fig. 9

BEARING ASSEMBLY OF A SWASH PLATE IN A STEERING GEAR COMPONENT AND SURGICAL INSTRUMENT

CROSS-REFERENCE TO RELATED APPLICATIONS

This application claims the benefit under 35 U.S.C. 119(a) to German Patent Application No. 10 2021 119 528.4, filed 28 Jul. 2021, the disclosure of which is incorporated herein by reference in its entirety.

BACKGROUND

An exemplary aspect relates to a bearing assembly for a swash plate in a steering gear component and to a surgical instrument which has such a bearing assembly.

Surgical instruments are known from the prior art which can be guided manually or by a robot and which have tools whose tool tip can be pivoted by means of various pivoting members engaging in one another. These pivot links are connected to a variety of steering wires or cords to provide fine control of the tool tip. A more even force distribution in all bending directions can be achieved with many thin steering wires compared to a few thicker steering wires.

Coupling such steering wires to a spatially adjustable disk which is arranged in an actuation unit on the proximal side and which is connected via a rod to a manually actuable control lever is known from U.S. Pat. No. 5,454,827, so that a movement of the spatially adjustable swash plate results in a corresponding relative movement of the distal-side pivoting elements and thus causes the tool tip to pivot.

The design of the drive for the steering wires with the spatially adjustable swash plate, on which the steering wires are mounted, has the advantage that this enables a spatially compact structure and only one component has to be moved in order to be able to address all steering wires.

U.S. Pat. No. 10,105,128 B2 discloses a surgical instrument with a mechanism to control the movement of a swash plate in two degrees of freedom via joint rods with drives on the proximal side, but the swash plate cannot be rotated in the instrument.

Also known is using a steering gear component in a surgical instrument to transmit drive setting angles to a swash plate for spatial alignment in two degrees of freedom/spatial directions, with the steering gear component being rotationally decoupled from the swash plate by a ball bearing. Cardan mounting of the swash plate on a main shaft transmits a rotational movement of the instrument shaft to the swash plate, so that the spatial position of the swash plate is determined by superimposing the movements of the steering gear component and the main shaft.

Depending on the structural design, it is not always possible to use a ball bearing.

Based on this state of the art, the object of the present disclosure is to provide an alternative to a ball bearing for a swash plate in a steering gear component, which mounts a swash plate in a steering gear component in a rotationally decoupled manner, without the transmission of movement being affected in two degrees of freedom/spatial directions toward the swash plate for controlling an instrument tool via steering wires.

This object is achieved by a bearing assembly having the features of claim 1.

The further object of providing a surgical instrument which has a bearing assembly for the spatially adjustable swash plate, which is an alternative to a ball bearing, is achieved by the surgical instrument having the features of independent claim 9.

Further developments and preferred embodiments of the bearing assembly and the surgical instrument are set out in the dependent claims.

According to a first embodiment of the bearing assembly for a swash plate in a steering gear component, the swash plate is arranged in a radial bearing such that it can rotate about an axis of rotation. This is present in a receiving opening of the steering gear component. According to an exemplary embodiment, the radial bearing is a sliding bearing and the bearing assembly has at least one axial securing device which is arranged axially adjacent to a first side of the swash plate and engages with the steering gear component.

In contrast to a conventionally used ball bearing, which allows rotation as the only degree of freedom, with a sliding bearing not only rotation is possible, but also a translational movement in the direction of the axis of rotation, especially with a corresponding force influence on the sliding bearing, which is avoided by the arrangement of the axial securing device. According to an exemplary embodiment, this prevents the swash plate from tilting and jamming in the steering gear component, so that the rotation of the swash plate in the steering gear component and thus the function of the bearing assembly is ensured.

In principle, it is conceivable for two axial securing devices to be used for axial securing on both sides, which secure the swash plate, which is slide-mounted in the steering gear component, from slipping or tilting from both sides.

In a preferred embodiment of the bearing assembly according to an exemplary embodiment, the swash plate has a radial, i.e., pointing in the radial direction, outer circumferential surface which is axially adjoined on one side by a circumferentially protruding ring web which faces away from the first side of the swash plate and adjoins the outer peripheral surface in an axial manner, i.e., pointing in axial direction, providing contact surface. The receiving opening has a first inner circumferential surface with a first diameter in a first hollow-cylindrical section and a second inner circumferential surface with a second diameter in a second hollow-cylindrical section, which is smaller than the first diameter, so that there is a ring shoulder between the first inner circumferential surface and the second inner circumferential surface, which provides an axial stop surface for the axial contact surface of the ring web, which is arranged in the first hollow cylindrical section. In this way, the swash plate can be fixed with the ring web on the side facing away from the axial securing device on the ring shoulder in the receiving opening. In this case, the ring web is arranged between the axial securing device and the axial stop surface, which is associated with reduced assembly work.

In a further embodiment of the bearing assembly according to an exemplary embodiment, it is provided that the sliding bearing, which is provided by a low-friction pair of materials, is present on at least one pair of friction surfaces, wherein a first pair of friction surfaces consists of the axial contact surface on the ring web of the swash plate and the axial stop surface in the receiving opening of the steering gear component, and a second pair of friction surfaces consists of the outer circumferential surface of the swash plate and the second inner circumferential surface of the receiving opening of the steering gear component. If the sliding bearing is on the first pair of friction surfaces consisting of an axial ring web contact surface and an axial receiving stop surface, the arrangement of a sliding disk is sufficient. If the sliding bearing is on the second pair of friction surfaces consisting of the outer peripheral surface of the swash plate and the second inner peripheral surface of the receiving opening, a sliding bearing bush is used. A sliding bearing bush with a corresponding one-sided collar can be used as a sliding bearing for both pairs of friction surfaces.

Optionally, the slide bearing can also extend to a pair of friction surfaces, which consists of an outer circumferential surface of the ring web and the first inner circumferential surface in the receiving opening of the steering gear component.

To form the slide bearing from the low-friction pair of materials, the respective contact surfaces of the friction partners from the pair of friction surfaces can each have a coating of a material from the pair of materials or consist of a material from the pair of materials. One friction partner can also consist of a material from the low-friction pair of materials and the other partner can have a coating on the contact surface made of the other material from the low-friction pair of materials. Additionally or alternatively, the sliding bearing can have lubrication. The sliding bearing can preferably have a sliding bearing bushing which is arranged in the receiving opening and has one of the materials from the low-friction pair of materials.

In a further embodiment, the bearing assembly can also provide a sliding bearing between the axial securing device and the first side of the swash plate, wherein the axial contact surfaces of the axial securing device and the swash plate facing one another also have a low-friction pair of materials.

In a further preferred embodiment of the bearing assembly, the axial securing device is provided by a thread ring with an external thread, with the steering gear component has a corresponding internal thread for engagement with the thread ring. The screw engagement advantageously makes it possible for permissible axial play that is predetermined for the swash plate to be adjustable by screw depth in the axial securing device, which is designed as a thread ring, in the steering gear component.

In a further embodiment, the swash plate of the bearing assembly is arranged on a shaft which defines the axis of rotation. For this purpose, the shaft has a ball section on which the shaft diameter is widened to form the ring contour, and the swash plate has a receiving recess therein which is at least partially adapted to the ring contour, so that the swash plate can be located about two axes perpendicular to the axis of rotation without axial offset on the shaft. In order to transmit a rotation or an angle of rotation of the shaft to the swash plate, there are two guide grooves on the ball section of the shaft in its outer surface, which extend diametrically and in the longitudinal direction of the shaft and into which two pins engage, which extend diametrically and, pointing radially inwards, are arranged on the swash plate or an inner side of the swash plate.

This advantageously results in a torsionally stiff connection between the shaft and the swash plate, which allows a transmission of the angle of rotation even with a large angular offset (±40° and more), but is still very compact and easy to manufacture and assemble.

According to yet another embodiment of the bearing assembly, the receiving recess in the swash plate can be spherical in shape corresponding to the ball section, whereby the receiving recess acts like a joint socket on both sides and the coupling is thus completely fixed axially. A two-piece design of the swash plate enables assembly in that the swash plate parts are mounted on the ball section to complete the swash plate.

According to an alternative embodiment, the receiving recess in the swash plate has a ball section and a cylindrical or widening section, so that the swash plate is only fixed on one side by the ball section and mounting on the ball section is made possible by the cylindrical or widening section when pushed onto the shaft in the direction of the ball section.

The surgical instrument according to an exemplary embodiment, which has a bearing assembly of a swash plate in a steering gear component, provides in a first embodiment that the bearing assembly is a bearing assembly according to an exemplary embodiment, since the bearing assembly according to an exemplary embodiment is particularly suitable for installation in a surgical instrument that has a main shaft and having a hollow shank coaxial with a longitudinal axis of the main shaft. At the proximal end of the shank (here the end closer to the actuator) is an actuation unit and at the distal end of the shank is a tool tip with a tool that can be actuated via an actuation element mounted in the shank in an axially displaceable manner and that also extends through a longitudinally axial through bore of the main shaft and is in operative connection with the actuation unit on the proximal side. The bearing assembly according to an exemplary embodiment is designed for the spatial alignment of the swash plate in relation to the main shaft in cooperation with a drive on the proximal side, so that a movement of the drive on the proximal side causes the tool tip to pivot.

With the steering gear component, the bearing assembly has an interface with the drive on the proximal side in order to transmit its adjustment angle to the swash plate for controlling the distal tool tip. The spatial alignment of the swash plate in relation to the main shaft by moving the drive on the proximal end causes the tool tip to pivot, which can be pivoted relative to the longitudinal axis of the shank via a joint mechanism. In one embodiment, the joint mechanism can consist of pivoting members arranged at the distal end of the shank, which are connected to the proximal-side drive via steering wires running in the longitudinal direction of the shank, wherein the steering wires are mounted on the swash plate, so that a movement of the proximal-side drive results in a corresponding relative movement of the distal-side pivoting members and thus the pivoting of the tool tip.

In a preferred embodiment of the bearing assembly of the surgical instrument according to an exemplary embodiment, the drive on the proximal side can be designed as a motorised drive with at least two drive wheels, e.g., driven gear wheels, between which the swash plate is arranged.

In this embodiment, the swash plate is coupled through the bearing assembly to a third gear wheel which engages with the two drive wheels, wherein the steering gear component is a steering ring which is non-rotatably coupled to the third gear, preferably being rotated on the axis of rotation of the third gear wheel by 180°, and a fourth gear wheel is arranged offset to the third gear wheel, which gear wheel engages with the two driven gear wheels, so that the gearing chain formed is closed to form a toothed ring, which ensures an evenly circulating force distribution.

BRIEF DESCRIPTION OF THE DRAWINGS

Further embodiments, as well as some of the advantages associated with these and other embodiments, will become apparent and better understood from the following detailed description with reference to the accompanying figures. Items or parts thereof that are substantially the same or similar may be given the same reference numbers. The figures are only a schematic representation of an exemplary embodiment.

Showing.

DETAILED DESCRIPTION

Figure 1:
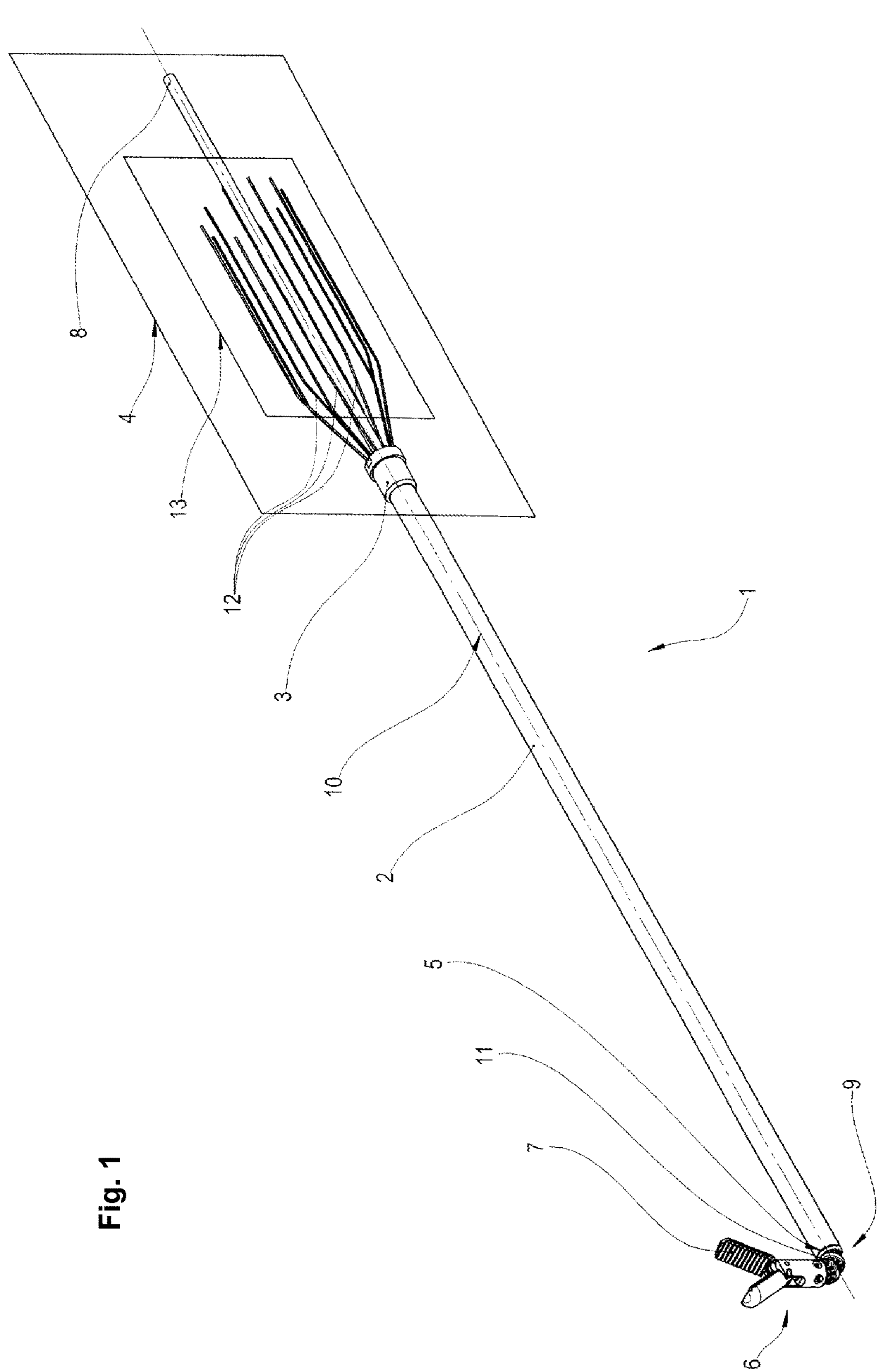
FIG. 1 a schematic perspective side view of a surgical instrument.

FIG. 1 schematically shows a surgical instrument 1 with a hollow shaft 2, an actuation unit 4 shown only schematically, arranged at the proximal end 3 of the shaft 2 and a tool tip 6 with a tool 7 arranged at the distal end 5 of the shaft 2, which has an axially displaceable mounted actuation element 8 in the shank 2 that can be actuated, which is in operative connection with the actuation unit 4 on the proximal side. The actuation unit 4 can be a manually actuable handling or a unit designed for robotic use, that is, one that can also be actuated without manual intervention. The tool 7 of the tool tip 6 can, for example, be a tool provided with jaw parts, as shown in FIG. 1, or act as an endoscope, an applicator or the like. The tool tip 6 can be pivoted relative to the longitudinal axis 10 of the shaft 2 via a joint mechanism 9, wherein the joint mechanism 9 consists of pivoting members 11 arranged at the distal end of the shaft 5, which are connected via guide wires 12 or guide ropes running in the longitudinal direction of the shaft 2 with a drive 13 arranged at the proximal end 3 of the shaft 2, which causes a movement of the drive 13 on the proximal side and corresponding relative movements of the pivoting members 11 on the distal side and thus a pivoting of the tool tip 6. Even if only the term steering wires 12 is used above and below, steering cables can also be used functionally, which is why the term steering wires 12 used should also be read and understood synonymously as a steering cable.

The actuation element 8, which is mounted so that it can be axially displaceable in the shaft 2 for actuating the tool 7, which consists of two jaw parts for example, is designed as a push/pull rod in the illustrated embodiment. In the medical instrument 1 according to an exemplary embodiment, the drive 13 for the steering wires 12 can preferably be designed as a motorised drive 13, which has a spatially adjustable swash plate 14, on which the steering wires 12 are mounted in such a way that a displacement of the swash plate 14 over the steering wires 12, preferably brought about by the motorised drive 13, causes the tool tip 6 to swivel, as is known from the prior art, e.g., U.S. Pat. No. 10,105,128 B2 or the swash plate bearing arrangement of FIG. 2.

By using a motorised drive 13 for the spatially adjustable disk 14, it is possible to control the steering wires 12 for pivoting the distal-side pivoting members 11 or the tool tip 6 precisely, sensitively in the smallest of steps and also reproducibly. In addition, the number of steering wires 12 to be used for a motorised drive 13 is irrelevant. The motorised drive 13 can, as known from the prior art according to FIG. 2, have two drive units with gear wheels 18 and 19 driven by motors, and bevel gears between which the swash plate 14 is arranged.

In the surgical instrument 1 according to FIG. 1 (combined with FIG. 2—state of the art—or FIG. 3 to 11—bearing assembly 40 according to an exemplary embodiment), a hollow main shank 21 is arranged in the shank 2 and extends coaxially to the longitudinal axis 10 of the shank 2, which can be rotated about the longitudinal axis 10 of the shank 2 and extends beyond the proximal end 3 of the shank 2 into the region of the motorised drive 13. The actuation element 8 for actuating the instrument 7 is mounted in an axially displaceable manner within this hollow main shaft 21.

Figure 7:
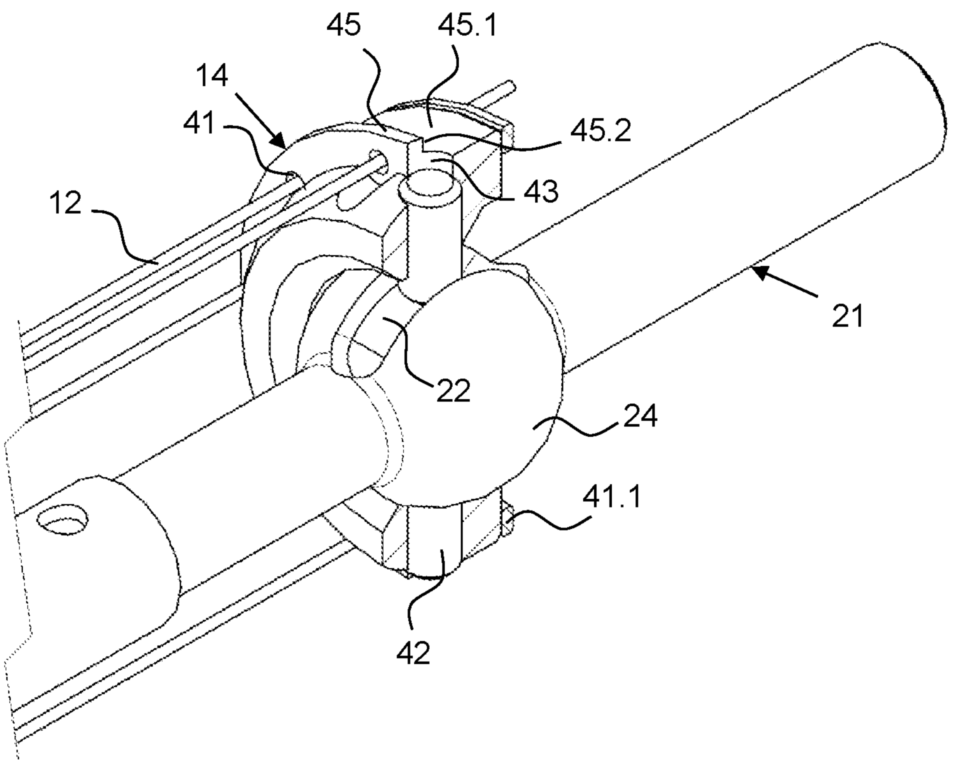
Figure 8:
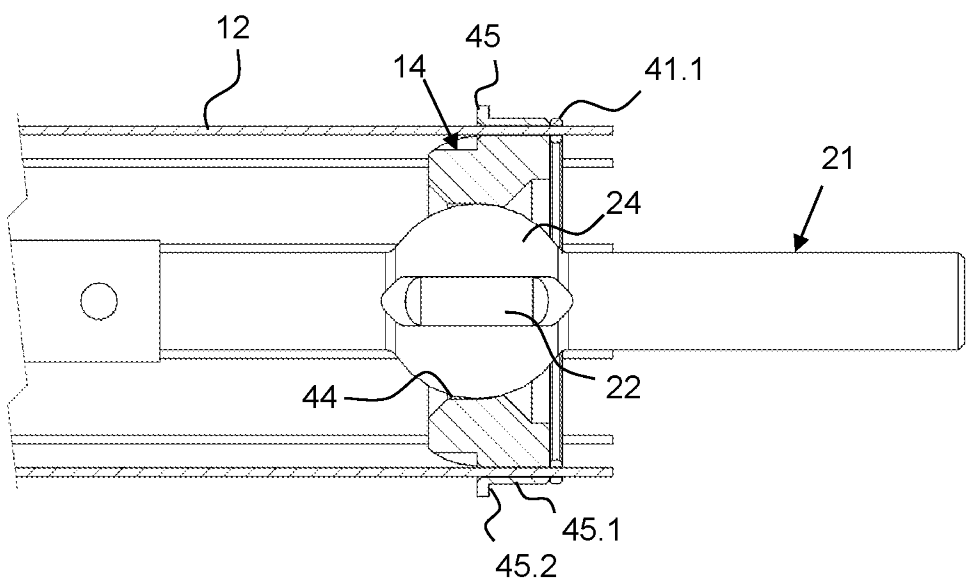

The steering wires 12 emerging from the shank 2 at the proximal end 3 of the shank 2 are guided at the distal end of the main shank 21 and can be fanned out via a serrated lock washer (not shown) arranged non-rotatably on the main shank 21, whereby the radial distance of the steering wires 12 from the longitudinal axis 10 of the shank 2 is increased. The steering wires 12 running parallel to the longitudinal axis 10 of the shank 2 behind such a serrated lock washer on the proximal side extend to the swash plate 14 to which the steering wires 12 are fixed. For this purpose, the swash plate 14 has an axially parallel through bore 41 for each steering wire 12, the steering wires 12 being fastened within the through bores 41 via grub screws 41.2 as in FIG. 2 or on the proximal side with a clamping disk 41.1, as shown in FIGS. 7 and 8, and can be fixed and non-positively connected to the swash plate 14.

The driven gear wheels 18 and 19 are coupled to a third gear wheel 30 which engages with the two gear wheels 18 and 19 and whose axis of rotation B intersects the central axis A of the driven gear wheels 18 and 19, as well as the longitudinal axis 10 of the shank 2. The third gear wheel 30 is also preferably designed as a bevel gear. Due to the three gear wheels 18, 19 and 30 engaging with each other, every movement of the two driven gear wheels 18 and 19 is transmitted directly to the swash plate 14 coupled to the third gear wheel 30, which causes the steering wires 12 to be actuated directly. In order to close the gearing chain formed by the gear wheels 18, 19 and 30 to form a closed toothed ring, which ensures an even distribution of power, a fourth gear wheel 31 is arranged on the axis of rotation B of the third gear wheel 30, offset by 180° with respect to the third gear wheel 30 in engagement with the two driven gear wheels 18 and 19, wherein the fourth gear wheel 31 is preferably also designed as a bevel gear.

Figure 2:
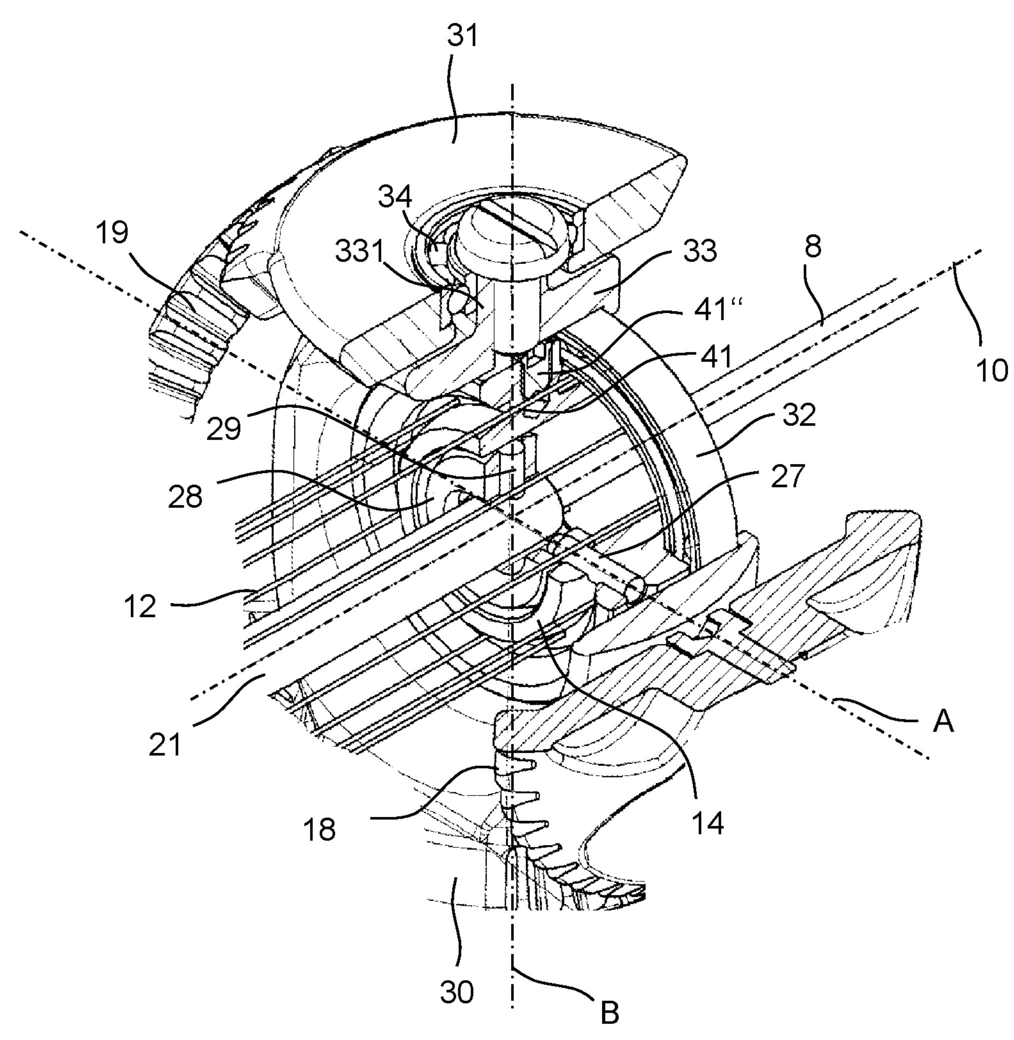
FIG. 2 a perspective detailed view of a swash plate bearing assembly from the prior art with a ball bearing for mounting the swash plate in a steering ring of the drive for the surgical instrument, FIG. 3 a side sectional view of a bearing assembly according to an exemplary embodiment, FIG. 4 a perspective view of the bearing assembly of FIG. 3, FIG. 5 a detailed sectional view D of the bearing assembly of FIG. 3 with an indicated sliding bearing bush, FIG. 6 an exploded view of the detailed sectional view D of FIG. 5 without the sliding bearing bush, FIG. 7 a perspective partial sectional view of the swash plate arranged on a ball section of a main shaft, which is designed for sliding bearing according to an exemplary embodiment in a steering ring of a drive for a surgical instrument, FIG. 8 a partially sectional plan view of the swash plate arranged on the ball portion of the main shaft of FIG. 7, and FIG. 9 a perspective view of a swash plate for sliding bearing in a steering ring of a drive for a surgical instrument and for arrangement on a ball section of the main shaft.

The swash plate 14 is in accordance with the known bearing assembly in FIG. 2 mounted via a (ball) bearing ring 32 in the steering ring 33, which is coupled in a rotationally fixed manner to the third gear wheel 30, in order to enable the swash plate 14 to rotate about the longitudinal axis 10 of the shank 2. The steering ring 33, which is coupled in a rotationally fixed manner to the third gear wheel 30, can be rotated freely on a bearing support 331 via a bearing ring 34 in relation to the fourth gear wheel 31, so that rotation of the fourth gear wheel 31 about its axis of rotation B does not cause the steering ring 33 and the swash plate 14 to rotate.

Figure 3:
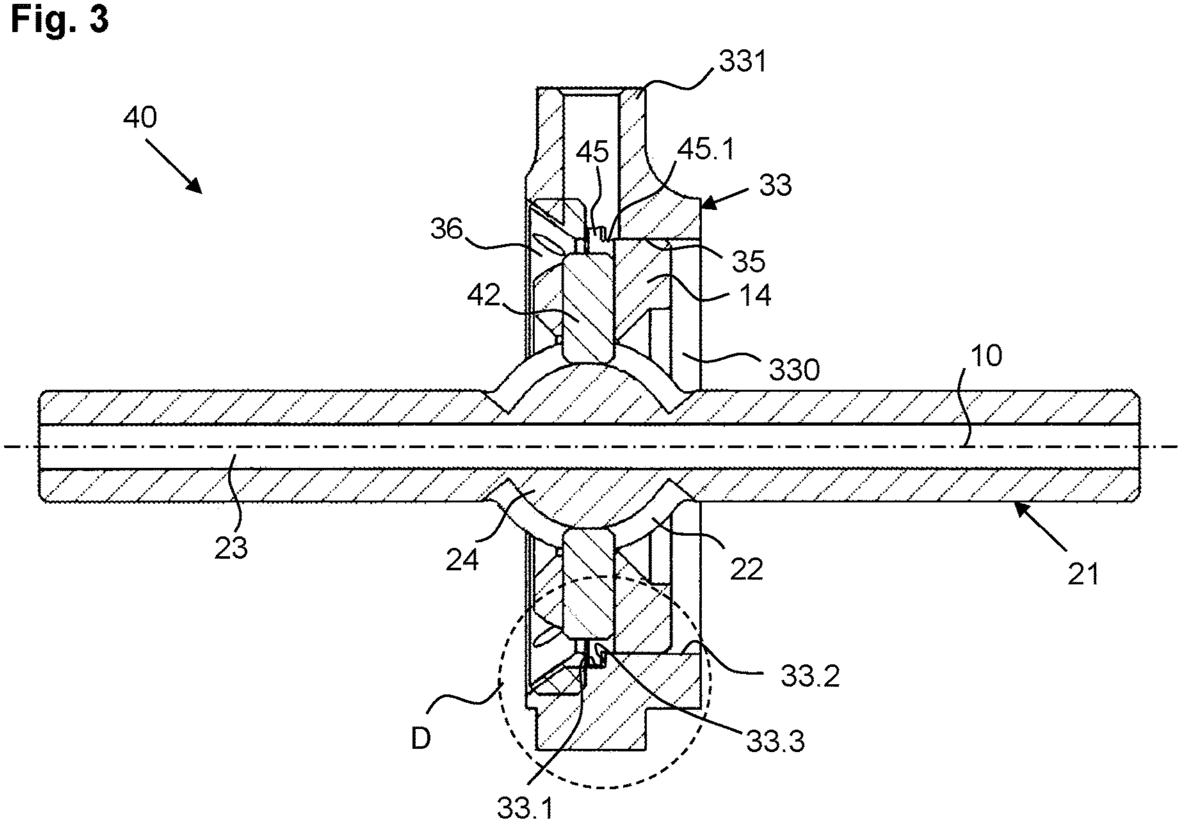
Figure 4:
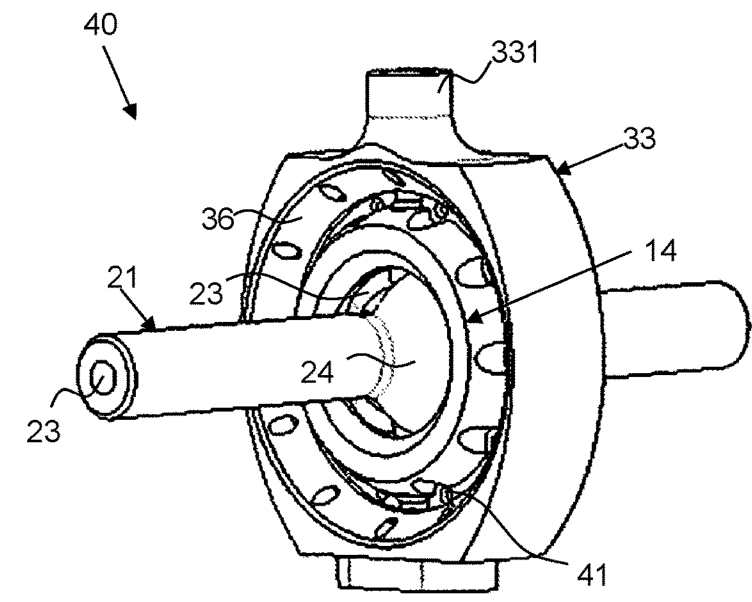
Figure 5:
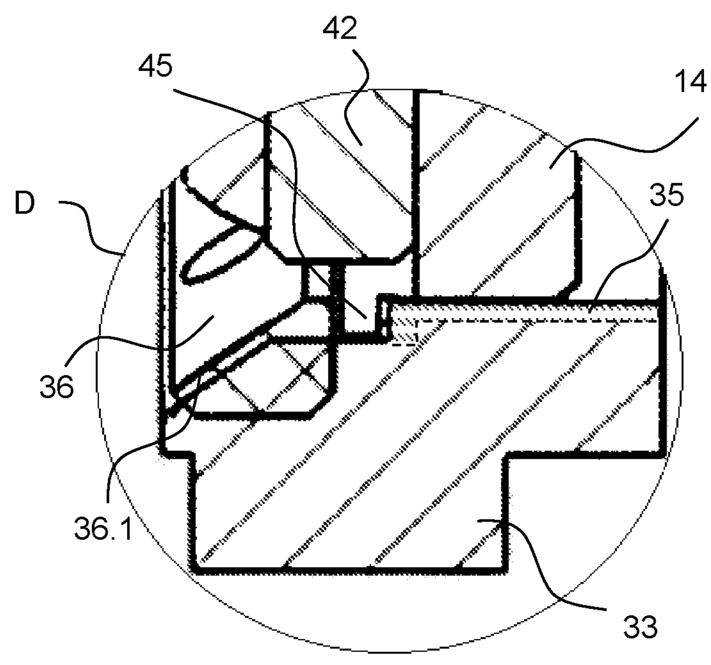

The above in relation to FIG. 2 described embodiments of the drive 13 for the spatial alignment of the swash plate 14 for controlling the tool tip by means of the steering wires 12 that also apply to a surgical instrument 1 according to an exemplary embodiment, which has a bearing assembly 40 according to an exemplary embodiment, as shown in FIG. 3 to 5.

The bearing assembly 40 according to an exemplary embodiment has a sliding bearing 35 instead of a ball bearing 32, which, unlike a ball bearing, fundamentally not only rotates, but in particular when a force acts on the sliding bearing 35, e.g., by the distal mechanics, it would also allow a translational movement in the direction of the axis of rotation 10 and thus a tilting or wedging of the swash plate 14 in relation to the steering ring 33, which could prevent the rotation of the swash plate 14 in the steering ring 33 and thus impair function. In order to prevent this tilting/wedging and seizing of the swash plate 14 when using a sliding bearing 35, the bearing assembly 40 according to an exemplary embodiment provides an axial securing device 36 which, as a counter bearing for sliding bearing 35, is arranged axially adjacent to the swash plate 14 in the receiving recess 330 of the steering ring 33 and engaged with the steering ring 33.

The axial securing of the swash plate 14 in the steering ring 33 requires a limitation on both sides, so that it is fundamentally conceivable to axially secure the swash plate 14, which is slide-mounted in the steering ring 33, between two axial securing devices 36 (not illustrated in the figures). In order to keep the installation effort low, the embodiment shown in FIG. 3 to 5 may be preferred, in which the axial securing device 36 fixes the swash plate 14 with a ring web 45 formed on the circumference thereof against a stop surface 33.3 formed in the receiving recess 330, as it becomes particularly clear in the detailed illustration D in FIGS. 5 and 6.

Figure 9:
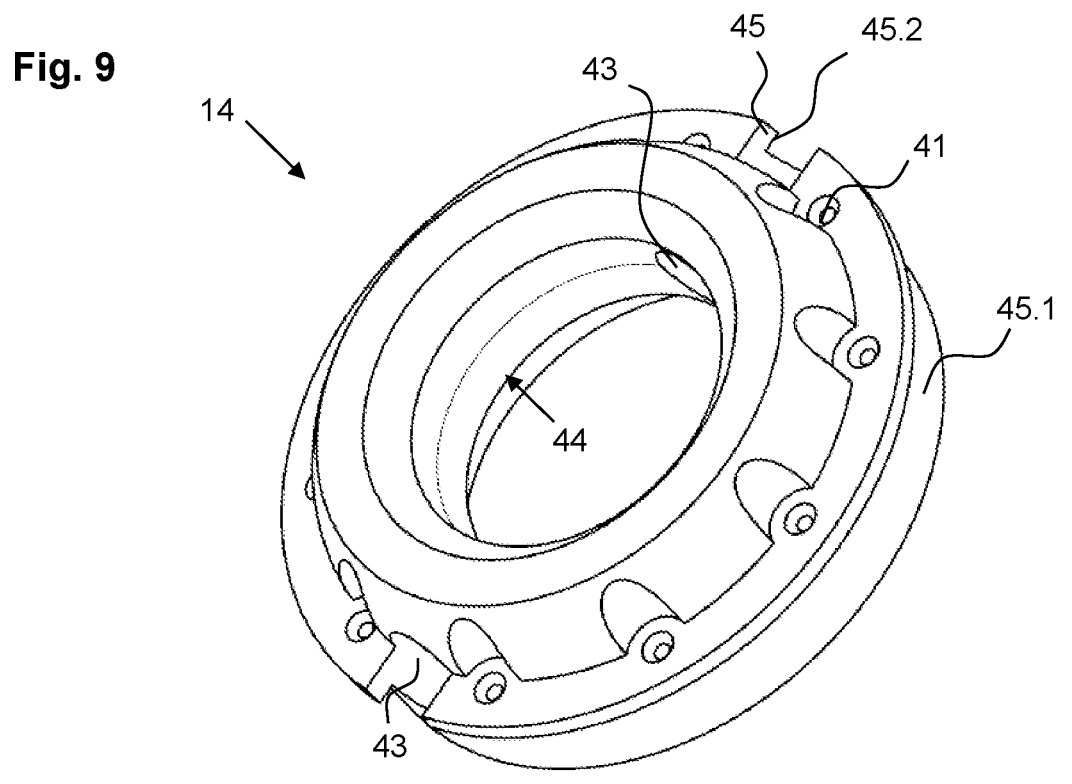

The swash plate 14, which is also shown in FIG. 7 to 9, has in the example shown an outer circumferential surface 45.1 and a ring web 45 which protrudes axially on one side and adjoins it on one side. This provides an axial contact surface 45.2 adjoining the outer circumferential surface 45.1, which faces away from the first side of the swash plate 14 on which the axial securing device 36 is arranged.

Figure 6:
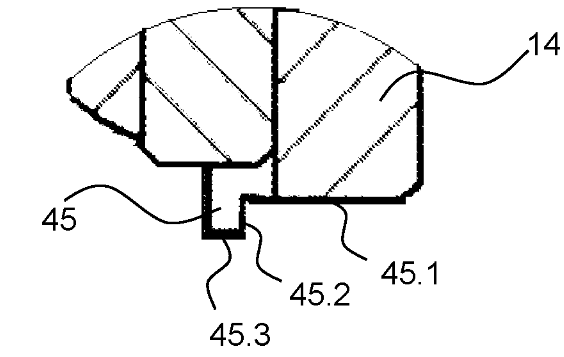
Figure 6:
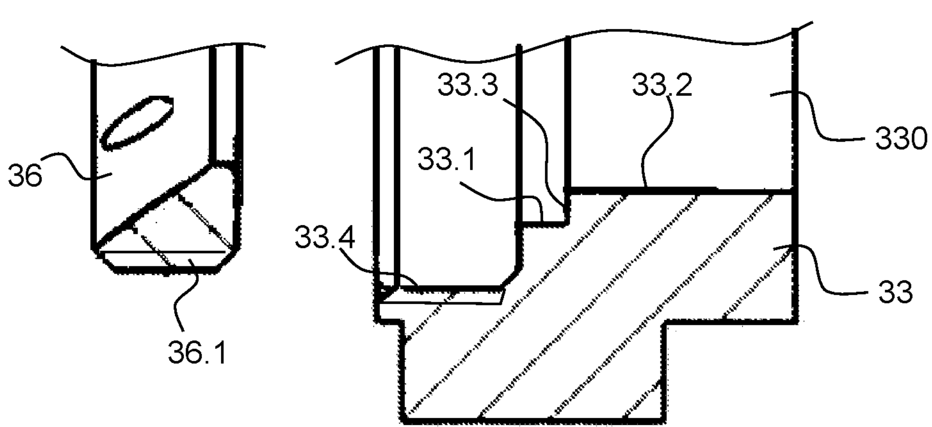

The receiving opening 330 in the steering ring 33 is designed with several hollow-cylindrical sections for receiving the swash plate 14, which is particularly well shown in FIG. 6. In a first hollow-cylindrical section, the receiving opening 330 has a first inner circumferential surface 33.1 with a first diameter and in a second hollow-cylindrical section a second inner circumferential surface 33.2 with a second diameter that is smaller than the first diameter, so that between the first inner circumferential surface 33.1 and the second inner circumferential surface 33.2 there is a ring shoulder, which provides the axial stop surface 33.3 for the axial contact surface 45.2 of the ring web 45, which is accommodated in the first hollow-cylindrical section. As shown in FIG. 5, the ring web 45 of the swash plate 14 is arranged secured between the axial securing device 36 and the axial stop surface 33.3.

There are no restrictions on the execution of the slide bearing 35. The slide bearing 35, which is defined by the contact surfaces of the friction partners, swash plate 14 and steering ring 33, can be provided by selecting a correspondingly low-friction pair of materials on the contacting surfaces of the swash plate 14 and the steering ring 33. Suitable pairs of materials can be, for example, stainless steel Nitronic® 1.3965-1.4021 (stainless steel, hardened); Polytetrafluoroethylene-1.4021 (stainless steel, hardened) or brass (CuZn39Pb3)-brass (CuZn39Pb3), without the scope of protection being limited thereto. That is, the contact surfaces can each have a coating made of a material from the pair of materials or the friction partners themselves can each consist of a material from the pair of materials. Additionally or alternatively, the sliding bearing 35 can have lubrication.

The surfaces of the friction partners that are in contact, on which the sliding bearing 35 is provided by a low-friction pair of materials, have a first pairing of friction surfaces consisting of the axial contact surface 45.2 on the ring web 45 of the swash plate 14 and the axial stop surface 33.3 in the receiving opening 330 of the steering ring 33. A second pair of friction surfaces, on which the slide bearing 35 is present, consists of the outer circumferential surface 45.1 of the swash plate 14 and the second inner circumferential surface 33.2 in the receiving opening 330 of the steering ring 33. The slide bearing 35 can preferably be replaced by a slide bearing bushing, which in FIG. 5 is indicated by dashed lines, which is arranged in the receiving recess 330 of the steering ring 33, and consists of a material of the low-friction pair of materials and the sliding contact surfaces on the axial stop surface 33.3 and the second inner circumferential surface 33.2 for the axial contact surface 45.2 and the outer circumferential surface 45.1 of the swash plate 14. The axial securing device 36 also prevents such a sliding bearing bush 35 from slipping out axially.

Optionally (not shown), the sliding bearing (coating, bushing) 35 can extend to a (third) pair of friction surfaces, which consists of an outer circumferential surface 45.3 of the ring web 45 of the swash plate 14 and the first inner circumferential surface 33.1 in the receiving opening 330 of the steering ring 33. Also not shown is the further possible sliding bearing between the axial securing device 36 and the first side of the swash plate 14 at the contacting surface sections.

In the example shown in the figures, the axial securing device 36 is designed as a thread ring 36 with an external thread 36.1, with the steering gear component 33 having a corresponding internal thread 33.4 in the receiving opening 330. With the axial securing device designed as a thread ring 36, the permissible play predetermined for the swash plate 14 can be adjusted by the screw depth of the thread ring 36 in the steering gear component 33. The adjustability of the bearing assembly 40 advantageously enables manufacturing and assembly tolerances to be compensated for in order to ensure the optimal functioning of the slide bearing 35. Furthermore, the sliding bearing surfaces can also be reduced to a minimum in order to further counteract the tilting of the swash plate 14 in the steering ring 33.

FIG. 7 to 9 illustrate the mounting of the swash plate 14 on the main shaft 21 of a surgical instrument 1 (see FIG. 1). The spatial orientation of the swash plate 14 for pivoting the tool tip 6 via the steering wires 12 is by superimposing the rotational position of the main shaft 21 and the adjustment angle of the drive on the proximal side (see FIG. 2). The bearing assembly is structurally simple and compact and easy to mount.

The main shaft 21 has a ball section 24 for the ball-joint mounting of the swash plate 14, on two guide grooves 22 extending in the longitudinal direction of the shaft 21 and introduced into the ball section 24 on both sides or diametrically. The swash plate 14 has a contoured receiving recess 44 that is at least partially adapted to the ball section 24 and from which two diametrically and radially inward-pointing pins 42 extend, which engage in the guide grooves 22 on the ball section 24 of the main shaft 21. To mount the pins 42, the swash plate 14 can have two diametrically radial passage bores 43, so that the pins 42 can be inserted from the outside of the swash plate 14 through the through hole 43 until they emerge on the inside of the swash plate 14 and radially protrude inward to the desired length. Alternatively, in embodiments that are not shown, the pins 42 can be fastened to the swash plate 14 in two diametrically radial blind bores running from the inside, or the pins 42 can be cohesively connected to the swash plate 14 on the inside, e.g., made in one piece.

The swash plate 14, which is a ball-bearing mounted in this way, can be moved from a neutral position, in which the swash plate 14 lies in a plane perpendicular to the longitudinal or rotational axis 10, to pivoted two spatial axes perpendicular about the rotational axis 10 (A, B, see FIG. 2). In addition, a rotation angle of the shaft 21 can be transferred to the swash plate 14 by the engagement of the pins 42 in the guide grooves 22.

The tilting or twisting of the swash plate 14 about one or both axes of rotation A, B relative to the longitudinal axis 10 of the shank 2 causes, via the steering wires 12, the tool tip 6 on the distal side to be pivoted in a corresponding manner relative to the longitudinal axis 10 of the shank 2. By transmitting a rotational movement of the main shank 21 about the longitudinal axis 10 of the shank 2 to the swash plate 14, the tool tip 6 coupled to the main shank 21 on the distal side can be rotated about the longitudinal axis 10 of the shank 2.

In FIG. 8 it can be seen that the receiving recess 44 in the example shown consists of a proximal-side spherical section and a distal-side cylindrical section, which allows the swash plate 14 to be mounted by sliding it on from the proximal-side end of the main shaft 21. As an alternative to a cylindrical section, a widening section (not shown) can be provided on the distal side. The swash plate 14 is only fixed on one side on the ball section by the ball section on the proximal side, but is held in place by the tension of the steering wires 12, which are passed through the passage openings 41 here and are fastened with a clamping ring 41.1 arranged on the proximal side, so that the swash plate 14 is fixed in the axial direction. In a modified embodiment, also not shown, the receiving recess 44 of the swash plate 14 can be formed corresponding to the ball section 24 without a cylindrical or widening section only with a ball section, so that the ball-joint bearing is completely fixed axially. However, this embodiment requires the swash plate 14 to be designed in at least two parts in order to enable assembly on the ball section 24.

LIST OF REFERENCE NUMBERS

1 Medical instrument
2 Shaft
3, 5 Proximal, distal end (shaft)
4 Actuation unit
6, 7 Tool tip, tool
8 Actuation element
9 Joint mechanism
10 Longitudinal axis
11 Pivoting member
12 Guide wire
13 Drive
14 Swash plate
18, 19 Gear wheel (driven)
21 Main shaft
22 Guide groove
23 Through bore
24 Ball section
27, 29 Bearing pin
28 Universal joint disk
30, 31 Third, fourth gear wheel
32, 34 Bearing ring
33, 330, 331 Steering ring, receiving opening, bearing support
33.1, 33.2 First inner circumferential surface, second inner circumferential surface
33.3, 33.4 Axial stop surface, thread
35 Sliding bearing (layer/bush)
36, 36.1 Axial locking device/thread ring, thread
40 Bearing assembly
41, 41.1, 41.2 Through bore, fastening disk, grub screw
42 Pin
43, 44 Receiving bore, receiving recess
45, 45.1 Ring shoulder, outer circumferential surface of swash plate
45.2, 45.3 Axial contact surface, outer circumferential surface ring shoulder

The invention claimed is:

1. A bearing assembly for a swash plate in a steering gear component, wherein the swash plate is arranged such that it can rotate about an axis of rotation in a radial bearing which is located in a receiving opening of the steering gear component, wherein the radial bearing is a sliding bearing and the bearing assembly has at least one axial securing device which is arranged axially adjacent to a first side of the swash plate and engages with the steering gear component.

2. The bearing assembly according to claim 1, wherein the swash plate has an outer circumferential surface and a circumferentially projecting ring web axially adjacent thereto on one side, the ring web providing an axial contact surface facing away from the first side of the swash plate and adjacent to the outer circumferential surface, and the receiving opening has a first inner circumferential surface with a first diameter in a first hollow-cylindrical section and a second inner circumferential surface with a second diameter in a second hollow-cylindrical section, which is smaller than the first diameter, so that between the first inner circumferential surface and the second inner circumferential surface there is a ring shoulder, which provides an axial stop surface for the axial contact surface of the ring web which is arranged in the first hollow-cylindrical section, wherein the ring web is arranged between the axial securing device and the axial stop surface.

3. The bearing assembly according to claim 2, wherein the sliding bearing is provided by a low-friction pair of materials on at least one pair of friction surfaces, wherein a first pair of friction surfaces consists of the axial contact surface and the axial stop surface and a second pairing of friction surfaces consists of the outer circumferential surface and the second inner circumferential surface, the sliding bearing optionally extending as far as a pair of friction surfaces consisting of an outer circumferential surface of the ring web and the first inner circumferential surface.

4. The bearing assembly according to claim 3, wherein the sliding bearing has a sliding bearing bush which is arranged in the receiving opening and has one of the materials from the low-friction pair of materials.

5. The bearing assembly according to claim 1, wherein the bearing assembly provides a sliding bearing between the axial securing device and the first side of the swash plate.

6. The bearing assembly according to claim 1, wherein the axial securing device is provided by a thread ring with an external thread, and the steering gear component has a corresponding internal thread,
wherein a predetermined allowable play for the swash plate can be adjusted by screw depth in the axial securing device in the steering gear component.

7. The bearing assembly according to claim 1, wherein the swash plate is arranged on a shaft which defines the axis of rotation, the shaft having a ball section for supporting the swash plate, and the swash plate having at least a partially adapted contoured receiving recess on the ball section, wherein
the ball section has two diametrically arranged guide grooves extending in the longitudinal direction of the shaft and
two pins arranged diametrically and radially inwards are arranged on the swash plate,
each pin engaging in one of the guide grooves, so that an angle of rotation of the shaft can be transferred to the swash plate.

8. The bearing assembly according to claim 7, wherein the receiving recess is of spherical design corresponding to the ball section, wherein the swash plate is of two-part design, or
the receiving recess has a spherical section and a cylindrical or flared section.

9. A surgical instrument with a bearing assembly of a swash plate in a steering gear component, wherein
the bearing assembly is a bearing assembly according to claim 1.

10. The surgical instrument according to claim 9, wherein the surgical instrument is designed with a main shaft running coaxially to a hollow shank and an actuation unit arranged at the proximal end of the shank and an actuation unit at the distal end of the tool tip arranged on the shank with a tool which can be actuated via an actuation element which is mounted in the shank in an axially displaceable manner and which extends through a longitudinally axial through bore in the main shaft and is in operative connection with the actuation unit on the proximal side, wherein the tool tip is pivotable via a joint mechanism relative to the longitudinal axis of the shank, and the joint mechanism has a drive in operative connection, which has the swash plate.

11. The surgical instrument according to claim 9, wherein the joint mechanism consists of pivoting members arranged at the distal end of the shaft which are connected to a drive on the proximal side via guide wires running in the longitudinal direction of the shaft, wherein a movement of the drive on the proximal side causes a corresponding relative movement of the pivoting members on the distal side and thus a pivoting of the tool tip, wherein the steering wires are mounted on the swash plate.

12. The surgical instrument according to claim 9, wherein the drive on the proximal side is designed as a motorised drive with at least two drive wheels, between which the swash plate is arranged.

13. The surgical instrument according to claim 12, wherein
the swash plate is coupled through the bearing assembly to a third gear wheel which engages with the two gear wheels, the steering gear component, being a steering ring which is non-rotatable, is coupled to the third gear wheel,
and wherein a fourth gear wheel, which engages with the two driven gear wheels, is preferably arranged on the axis of rotation of the third gear wheel offset by 180° to the third gear wheel.

14. An assembly comprising:
a bearing assembly,
a swash plate, and
a steering gear,
wherein the swash plate is configured to rotate about an axis of rotation within a radial bearing, the radial bearing located in a receiving opening of the steering gear, and
wherein the radial bearing is a sliding bearing, and the bearing assembly has at least one axial securing device which is arranged axially adjacent to a first side of the swash plate and engages with the steering gear.

15. The bearing assembly of claim 14, wherein the swash plate has an outer circumferential surface and a circumferentially projecting ring web axially adjacent thereto on one side, the ring web providing an axial contact surface facing away from the first side of the swash plate and adjacent to the outer circumferential surface, and
the receiving opening has a first inner circumferential surface with a first diameter in a first hollow-cylindrical section and a second inner circumferential surface with a second diameter in a second hollow-cylindrical section, which is smaller than the first diameter, so that between the first inner circumferential surface and the second inner circumferential surface there is a ring shoulder, which provides an axial stop surface for the axial contact surface of the ring web which is arranged in the first hollow-cylindrical section, wherein the ring web is arranged between the axial securing device and the axial stop surface.

16. The assembly of claim 15, wherein the sliding bearing is provided by a low- friction pair of materials on at least one pair of friction surfaces, wherein a first pair of friction surfaces includes the axial contact surface and the axial stop surface and a second pairing of friction surfaces includes the outer circumferential surface and the second inner circumferential surface,
the sliding bearing optionally extending as far as a pair of friction surfaces consisting of an outer circumferential surface of the ring web and the first inner circumferential surface.

17. The assembly of claim 16, wherein the sliding bearing has a sliding bearing bush which is arranged in the receiving opening and has one of the materials from the low-friction pair of materials.

18. The assembly of claim 14, wherein the bearing assembly provides a sliding bearing between the axial securing device and the first side of the swash plate.

19. The assembly of claim 14, wherein:
the axial securing device is provided by a thread ring with an external thread, and the steering gear has a corresponding internal thread,
wherein a predetermined allowable play for the swash plate can be adjusted by screw depth in the axial securing device in the steering gear.

20. The assembly of claim 14, wherein:
the swash plate is arranged on a shaft which defines the axis of rotation, the shaft having a ball section for supporting the swash plate, and the swash plate having at least a partially adapted contoured receiving recess on the ball section, wherein
the ball section has two diametrically arranged guide grooves extending in the longitudinal direction of the shaft and two pins arranged diametrically and radially inwards are arranged on the swash plate, each pin engaging in one of the guide grooves, so that an angle of rotation of the shaft can be transferred to the swash plate.

* * * * *